(12) United States Patent
Hansen et al.

(10) Patent No.: US 12,122,852 B2
(45) Date of Patent: Oct. 22, 2024

(54) 14-3-3 TARGETING PEPTIDES FOR CANCER TREATMENT

(71) Applicants: Creighton University, Omaha, NE (US); The Board of Regents of the University of Nebraska, Omaha, NE (US)

(72) Inventors: Laura Hansen, Bellevue, NE (US); Sandor Lovas, Omaha, NE (US); Nicholas Palermo, Omaha, NE (US)

(73) Assignees: CREIGHTON UNIVERSITY, Omaha, NE (US); NUTECH VENTURES, Lincoln, NE (US)

( * ) Notice: Subject to any disclaimer, the term of this patent is extended or adjusted under 35 U.S.C. 154(b) by 0 days.

(21) Appl. No.: 18/076,033

(22) Filed: Dec. 6, 2022

(65) Prior Publication Data
US 2023/0312645 A1    Oct. 5, 2023

Related U.S. Application Data

(62) Division of application No. 16/870,253, filed on May 8, 2020, now Pat. No. 11,518,784.

(60) Provisional application No. 62/845,156, filed on May 8, 2019.

(51) Int. Cl.
| | |
|---|---|
| C07K 7/08 | (2006.01) |
| A61K 9/06 | (2006.01) |
| A61K 9/107 | (2006.01) |
| A61K 38/00 | (2006.01) |
| A61P 35/00 | (2006.01) |
| C07K 5/117 | (2006.01) |

(52) U.S. Cl.
CPC ............. *C07K 5/1024* (2013.01); *A61K 9/06* (2013.01); *A61K 9/107* (2013.01); *A61P 35/00* (2018.01); *C07K 7/08* (2013.01); *A61K 38/00* (2013.01)

(58) Field of Classification Search
CPC .......... C07K 5/1024; C07K 7/08; A61K 9/06; A61K 9/107; A61K 38/00; A61P 35/00
See application file for complete search history.

(56) References Cited

U.S. PATENT DOCUMENTS

| | | | |
|---|---|---|---|
| 4,966,848 A | 10/1990 | Smith et al. | |
| 5,223,421 A | 6/1993 | Smith et al. | |
| 5,837,218 A | 11/1998 | Peers et al. | |
| 8,298,775 B2* | 10/2012 | Ryu | C07K 16/40 |
| | | | 435/7.1 |
| 2003/0032617 A1 | 2/2003 | Harel et al. | |
| 2013/0129725 A1 | 5/2013 | Fachin et al. | |
| 2017/0312249 A1 | 11/2017 | Woodcock et al. | |
| 2018/0291423 A1 | 10/2018 | Ruijtenbeek et al. | |

FOREIGN PATENT DOCUMENTS

| | | |
|---|---|---|
| WO | 2016184999 A1 | 11/2016 |
| WO | 2018178215 A1 | 10/2018 |

OTHER PUBLICATIONS

Ardito et al., "The crucial role of protein phosphorylation in cell signaling and its use as targeted therapy," International Journal of Molecular Medicine, 2017, 40: 271-280. (Year: 2017).
Holmes, Thomas R. et al., 'CDC25A suppression of apoptosis in cutaneoussquamous cell carcinoma depends on 14-3-3ε', Proceedings: AACR AnnualMeeting 2018, Jul. 2018(Publication date), vol. 78, No. 13 Supplement, LB-190abstract.
Notification of Transmittal of the Internationalsearch Report and the Written Opinion of the International Searching Authority, or the Declaration dated Aug. 26, 2020 for App. No. PCT/US20/32089.
Woodcock, Joanna M. et al., 'Destabilisation of dimeric 14-3-3 proteins as anovel approach to anti-cancer therapeutics', Oncotarget, May 4, 2015, vol. 6, No. 16, pp. 14522-14536pp. 14522-14531.

* cited by examiner

*Primary Examiner* — Julie Ha
(74) *Attorney, Agent, or Firm* — Mallory M. Henninger; Advent, LLP (57) ABSTRACT

Systems and methods for treatment of squamous cell carcinoma or other cancer utilizing targeting peptides are described. The targeting peptides interact with SCC cells or other cancerous cells to block or interfere with 14-3-3ε heterodimerization or CDC25A binding to 14-3-3ε. A peptide composition embodiment includes, but is not limited to, at least one of a first targeting peptide comprising a structure of Trp-Tyr-Trp-Lys-NH$_2$ (SEQ ID NO: 1), a second targeting peptide comprising a structure of phospho-Ser178; Ac-Thr-Gln-Arg-Gln-Asn-Ser-(PO$_3^{2-}$)-Ala-Pro-Arg-Met-Leu-Ser-Ser-Asn-NH$_2$ (SEQ ID NO: 2), and a third targeting peptide comprising a structure of phospho-Thr507 residue; Ac-Arg-Thr-Lys-Ser-Arg-Thr(PO$_3^{2-}$)-Trp-Ala-Gly-Glu-Lys-Ser-Lys-Arg-NH$_2$ (SEQ ID NO: 3).

5 Claims, 4 Drawing Sheets
(3 of 4 Drawing Sheet(s) Filed in Color)
Specification includes a Sequence Listing.

14-3-3 TARGETING PEPTIDES FOR CANCER TREATMENT

CROSS-REFERENCE TO RELATED APPLICATIONS

The present application is a continuation under 35 U.S.C. § 120 of U.S. patent application Ser. No. 16/870,253, filed May 8, 2020, and titled "14-3-3 TARGETING PEPTIDES FOR CANCER TREATMENT," which claims the benefit under 35 U.S.C. § 119(e) of U.S. Provisional Application Ser. No. 62/845,156, filed May 8, 2019, and titled "14-3-3 TARGETING PEPTIDES FOR CANCER TREATMENT." U.S. Patent Application Serial Nos. 62/845,156; Ser. No. 16/870,253 are herein incorporated by reference in their entireties.

INCORPORATION OF SEQUENCE LISTING

The sequence listing contained in the file named "100900144USU1D1-Replacement-Sequence-Listing-6-20-2023-ST26.xml", which is 7.39 kilobytes in size (measured in MS-Windows®), contains 3 sequences, and which was created on Jun. 20, 2023, is contemporaneously filed with this specification by electronic submission (using the United States Patent Office EFS-Web filing system) and is incorporated herein by reference in its entirety.

BACKGROUND

The skin is the largest organ of the body, with an average total area of 20 square feet. It serves many important functions including protection from external assaults, sensation of heat and cold, regulation of body temperature, water retention, storage and synthesis of vitamin D and excretion. These functions are supported by the skin's structure, which is composed of three primary layers: The epidermis, dermis and subcutaneous. The outermost epidermis and underlying dermis are separated by a basement membrane, with the dermis resting on a subcutaneous tissue of fat that attaches the skin to the underlying muscles and bones. The structure of the skin is reliant upon a closely regulated process of cell proliferation, differentiation, and death that helps to preserve not only the structural integrity of the skin, but also its ability to protect the body from external assaults and maintain bodily homeostasis. As such, any disturbance in the regulation of cell division or cell death has the potential to lead to cancer or other pathologies.

SUMMARY

Systems and methods for treatment of squamous cell carcinoma or other cancer utilizing targeting peptides are described. A peptide composition embodiment includes, but is not limited to, at least one of a first targeting peptide comprising a structure of Trp-Tyr-Trp-Lys-NH$_2$ (SEQ ID NO: 1), a second targeting peptide comprising a structure of phospho-Ser178; Ac-Thr-Gln-Arg-Gln-Asn-Ser-(PO$_3^{2-}$)-Ala-Pro-Arg-Met-Leu-Ser-Ser-Asn-NH$_2$ (SEQ ID NO: 2), and a third targeting peptide comprising a structure of phospho-Thr507 residue; Ac-Arg-Thr-Lys-Ser-Arg-Thr (PO$_3^{2-}$)-Trp-Ala-Gly-Glu-Lys-Ser-Lys-Arg-NH$_2$ (SEQ ID NO: 3).

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The patent or application file contains at least one drawing executed in color. Copies of this patent or patent application publication with color drawing(s) will be provided by the Office upon request and payment of the necessary fee.

The Detailed Description is described with reference to the accompanying figures. In the figures, the use of the same reference numbers in different instances in the description and the figures may indicate similar or identical items.

DETAILED DESCRIPTION

Overview

Skin cancer is the most common form of cancer, accounting for 40% of all cases globally. Malignancy is associated with genetic instability that results from DNA mutations. In skin cancers, much if not all of the damage to DNA is a result of chronic exposure to UV radiation. Skin cancers can be broadly segregated into two groups, melanoma and the much more common non-melanoma skin cancers (NMSC). Basal cell carcinoma (BCC) is the most prevalent form of NMSC making up 80% of all NMSC cases. BCC arises from the keratinocytes of the stratum basale and are slow growing, non-life threatening, and very rarely metastasize beyond the original tumor site as shown by a rate of metastasis below 0.1%. Squamous cell carcinoma (SCC) is the second most frequent form of NMSC and can become deadly if unattended.

Contrary to the low metastasis rate of BCCs, SCCs have a 5% chance to metastasize of which 40% will result in death. The location of SCCs can determine the aggressiveness of the cancer, as primary tumors in sun-exposed areas of the skin only have a 5% chance of metastasis while those that originate in non-sun-exposed areas of the skin have a 20% or more rate of metastasis. Additionally, the rate of SCC is upwards of 250 times higher in those with a compromised immune system, such as organ transplant recipients, and these SCCs present a much more aggressive phenotype.

Treatments for SCC typically include invasive surgical procedures, such as surgical excision. Treatments for other NMSCs can have negative side effects, including the development of different types of NMSCs. For example, vismodegib is a chemotherapy drug used to treat BCC that can lead to the development of SCCs during treatment.

Accordingly, the present disclosure is directed, at least in part, to systems and methods for treatment of SCCs or other cancers utilizing synthetic targeting peptides. The targeting peptides target and interact with specific 14-3-3 proteins that typically regulate protein stability, localization, or activity within cells through binding mechanisms with client proteins, such as cell cycle regulator cell division cycle 25 (CDC25) phosphatases. CDC25 phosphatases (e.g., CDC25A, CDC25B, and CDC25C) and 14-3-3 proteins (e.g., isoforms β, ε, η, σ, θ, γ and ζ) have been implicated in various cancers where they often promote cell division or survival. Surprisingly, research conducted revealed that CDC25A overexpression or silencing did not impact proliferation in SCC cells, but instead, CDC25A suppressed apoptosis in a manner dependent on 14-3-3 and cytoplasmic localization. Both CDC25A and 14-3-3ε activated Akt, inhibited pro-apoptotic protein Bcl2-associated death promoter (BAD), and increased Survivin, leading to increased SCC cell survival. The targeting peptides of the present disclosure were designed and synthesized to block 14-3-3ε heterodimerization or CDC25A binding to 14-3-38. The targeting peptides of the present disclosure successfully disrupted CDC25A binding to 14-3-3ε and 14-3-3ε heterodimerization, reduced SCC cell viability, increased apoptosis, and decreased active Akt and Survivin levels, providing a mechanism for skin cancer treatment.

EXAMPLE IMPLEMENTATIONS

In embodiments, the targeting peptide includes one or more of a first targeting peptide, a second targeting peptide, and a third targeting peptide to at least one of bind to 14-3-3ε heterodimerization binding sites or bind to one or more of two 14-3-3 binding sites of CDC25A. In embodiments, the first targeting peptide includes peptide ES1P2 (Trp-Tyr-Trp-Lys-NH$_2$ (SEQ ID NO: 1)) and has an IC$_{50}$ of 20.6 μM in SCC cells to reduce 14-3-3ε heterodimerization and increase apoptosis of SCC cells. In embodiments, the second targeting peptide includes peptide pS (phospho-Ser178; Ac-Thr-Gln-Arg-Gln-Asn-Ser-(PO$_3^{2-}$)-Ala-Pro-Arg-Met-Leu-Ser-Ser-Asn-NH$_2$ (SEQ ID NO: 2)) and has an IC$_{50}$ of 29 μM to induce SCC cell death and block 14-3-3ε binding to CDC25A. In embodiments, the third targeting peptide includes peptide pT (phospho-Thr507 residue; Ac-Arg-Thr-Lys-Ser-Arg-Thr(PO$_3^{2-}$)-Trp-Ala-Gly-Glu-Lys-Ser-Lys-Arg-NH$_2$ (SEQ ID NO: 3)) and has an IC$_{50}$ of 22.1 μM to induce SCC cell death and block 14-3-3ε binding to CDC25A.

In embodiments, one or more targeting peptides are included in a peptide composition having activity against squamous cell carcinoma survival. For example, the peptide composition can include one or more of ES1P2, pS, and pT. The peptide composition can include a pharmaceutically acceptable carrier to facilitate delivery of the peptide composition to one or more regions of an individual subject containing SCC cells. For example, the pharmaceutically acceptable carrier is suitable for administration via at least one of administration via injection, aerosol administration, administration via inhalation, oral administration, systemic IV application, ocular administration, and rectal administration.

The one or more targeting peptides can include a peptide having the formula X—R$^1$—R$^2$—R$^3$—R$^4$—Y, where X represents hydrogen, acetyl, or propionyl group, R$^1$ through R$^4$ represent all possible combinations of 19 standard L-amino or D-amino acid residues (excluding Cys): Ala, Arg, Asn, Asp, Gln, Glu, Gly, His, Ile, Leu, Lys, Met, Phe, Pro, Ser, Thr, Trp, Tyr, Val, and Y represents —OH, amide, methylamide or ethylamide groups. The one or more targeting peptides can include a peptide having the formula X—R$^1$—R$^2$—R$^3$—R$^4$—R$^5$—R$^6$—Y, where X represents hydrogen, acetyl, or propionyl group, R$^1$ through R$^6$ represent all possible combinations of 19 standard L-amino or D-amino acid residues (excluding Cys): Ala, Arg, Asn, Asp, Gln, Glu, Gly, His, Ile, Leu, Lys, Met, Phe, Pro, Ser, Thr, Trp, Tyr, Val, and Y represents —OH, amide, methylamide or ethylamide groups. The one or more targeting peptides can include peptide ES1P2 (Trp-Tyr-Trp-Lys-NH$_2$ (SEQ ID NO: 1)) with a connection at a carboxy terminal end to a hex-Gly spacer connected to peptide pS (phospho-Ser178; Ac-Thr-Gln-Arg-Gln-Asn-Ser-(PO$_3^{2-}$)-Ala-Pro-Arg-Met-Leu-Ser-Ser-Asn-NH$_2$ (SEQ ID NO: 2)). The one or more targeting peptides can include peptide ES1P2 (Trp-Tyr-Trp-Lys-NH$_2$ (SEQ ID NO: 1)) with a connection at a carboxy terminal end to a hex-Gly spacer connected to peptide pT (phospho-Thr507 residue; Ac-Arg-Thr-Lys-Ser-Arg-Thr(PO$_3^{2-}$)-Trp-Ala-Gly-Glu-Lys-Ser-Lys-Arg-NH$_2$ (SEQ ID NO: 3)).

In embodiments, the peptide composition can include one or more additional ingredients including, but not limited to, pharmaceutical filler ingredients.

In some embodiments, the peptide compositions described herein are adapted for topical application. Such compositions can include the peptide conjugated together with a carrier to facilitate topical application. Such a composition may be, for example, in the form of solutions, suspensions, emulsions, lotions, creams, microemulsions, nanoemulsions, emulgels, gels, and the like. Compositions described herein may also extend to patches and plasters for application to skin and incorporating peptides in a form such that it will be released into the skin.

In some embodiments, peptide compositions described herein include pharmaceutically and/or dermatologically acceptable excipients including, but not limited to, one or more of carriers, emulsifiers, coemulsifiers, permeation or penetration enhancers, solvents, co-solvents, emollients, antioxidants, preservatives, buffering agents, gelling or thickening agents, polymers, surfactants, soothing agents, pH modifiers, solubilizers, humectants, emollients, moisturizers, oily bases, and the like.

The term "carrier" or "vehicle" denotes organic or inorganic ingredients, natural or synthetic, with which an active ingredient is combined to facilitate application of a composition. Examples of carriers include, but not limited to, water, acetone, alone or in combination with materials such as silicone fluids. In certain embodiments, the carrier can comprise, in addition to water, water-immiscible substances such as any pharmaceutically acceptable fatty esters of natural fatty acids, triglycerides of animal or vegetable, medium chain triglycerides, mixtures of mono-, di- and/or triglycerides, waxes, hydrogenated vegetable oils, and mixtures thereof.

Examples of emulsifiers include, but not limited to, disodium cocoampho diacetate, oxyethylenated glyceryl cocoate (7 EO), PEG-20 hexadecenyl succinate, PEG-15 stearyl ether, ricinoleic monoethanolamide monosulfosuccinate salts, oxyethylenated hydrogenated ricinoleic triglyceride containing 60 ethylene oxide units such as the products marketed by BASF under the trademarks CREMOPHOR® RH 60 or CREMOPHOr® RH 40 (polyoxyl 40 hydrogenated castor oil), polymers such as poloxamers, which are block copolymers of ethylene oxide and propylene oxide, and the nonsolid fatty substances at room temperature (that is to say, at temperatures ranging from about 20 to 350° C.) such as sesame oil, sweet almond oil, apricot stone oil, sunflower oil, octoxyglyceryl palmitate (or 2-ethylhexyl glyceryl ether palmitate), octoxyglyceryl behenate (or 2-ethylhexyl glyceryl ether behenate), dioctyl adipate, and tartrates of branched dialcohols. Sorbitan fatty acid esters are a series of mixtures of partial esters of sorbitol and its mono- and dianhydrides with fatty acids. Sorbitan esters include products marketed as ARLACEL® 20, ARLACEL 40, ARLACEL 60, ARLACEL 80, ARLACEL83, ARLACEL 85, ARLACEL 987, ARLACEL C, PEG-6 stearate and glycol stearate and PEG-32 stearate (TEFOSE® 63), and PEG-6 stearate and PEG-32 stearate (TEFOSE® 1500), glyceryl stearate and PEG 100 stearate (TEFOSE® 165) and any mixtures thereof. Polyethylene glycol ethers of stearic acid are in another group of emulsifiers that can be used in the emulsions. Examples of polyethylene glycol ethers of stearic acid include, but not limited to, steareth-2, steareth-4, steareth-6, steareth-7, steareth-10, steareth-11, steareth-13, steareth-15, steareth-20, polyethylene glycol ethers of stearyl alcohol (steareth 21), and any mixtures thereof. Other emulsifiers include sodium lauryl sulphate, cetyl trialkyl ammonium bromide, polyoxyethylene sorbitan fatty acid esters, and any mixtures thereof.

Nonionic emulsifiers include those that can be broadly defined as condensation products of long chain alcohols, e.g., C8-30 alcohols, with sugar or starch polymers, i.e., glycosides. Various sugars include, but not limited to, glucose, fructose, mannose, and galactose, and various long chain alcohols include, but are not limited to, decyl alcohol, cetyl alcohol, stearyl alcohol, lauryl alcohol, myristyl alcohol, oleyl alcohol, and any mixtures thereof. Other useful nonionic emulsifiers include condensation products of alkylene oxides with fatty acids such as alkylene oxide esters of fatty acids. Other nonionic surfactants are the condensation products of alkylene oxides with 2 moles of fatty acids such as alkylene oxide diesters of fatty acids.

Emulsifiers can also include any of a wide variety of cationic, anionic, zwitterionic, and amphoteric surfactants that are known in the art. Examples of anionic emulsifiers include, but are not limited to, alkyl isethionates, alkyl and alkyl ether sulfates and salts thereof, alkyl and alkenyl ether phosphates and salts thereof, alkyl methyl taurates, and soaps (e.g., alkali metal salts and sodium or potassium salts) of fatty acids. Examples of amphoteric and zwitterionic emulsifiers include those which are broadly described as derivatives of aliphatic secondary and tertiary amines in which the aliphatic radical can be straight or branched chain, wherein one of the aliphatic substituents contains from about 8 to about 22 carbon atoms and one contains an anionic water solubilizing group, e.g., carboxy, sulfonate, sulfate, phosphate, or phosphonate. Specific examples include, but not limited to, alkylimino acetates, iminodialkanoates and aminoalkanoates, imidazolinium and ammonium derivatives. Other suitable amphoteric and zwitterionic emulsifiers include betaines, sultaines, hydroxysultaines, alkyl sarcosinates, and alkanoyl sarcosinates.

Silicone emulsifiers can include organically modified organopoly siloxanes, sometimes called silicone surfactants. Useful silicone emulsifiers can include dimethicone copolyols. These materials are polydimethyl siloxanes, which have been modified to include polyether side chains such as polyethylene oxide chains, polypropylene oxide chains, mixtures of these chains, and polyether chains containing moieties derived from both ethylene oxide and propylene oxide.

Co-emulsifiers include, but not limited to, polyoxylglycerides such as oleoyl macrogolglycerides (LABRAFIL® M 1944CS), linoleoyl macrogolglycerides (LABRAFIL® M 2125CS), caprylocaproyl macrogolglycerides (LABRASOL®), cetyl alcohol (and) ceteth-20 (and) steareth-20 (EMULCIRE™ 61 WL 2659), glyceryl stearate (and) PEG-75 stearate (GELOT® 64), d-alpha tocopheryl polyethylene glycol 1000 succinate (TPGS) and any mixtures thereof.

The term "solvent" refers to components that aid in the dissolution of the drug in the formulation. Solvents serve to maintain a solution of the drug in the composition. Some solvents can also enhance percutaneous penetration of drug and/or act as humectants. Solvents that can be used in the present peptide compositions can include water-immiscible substances such as fatty esters of natural fatty acids, triglycerides of animal or vegetable, medium chain triglycerides, mixtures of mono-, di- and/or triglycerides, waxes, hydrogenated vegetable oils, and mixtures thereof. Some specific examples include, but not limited to, castor oil, isopropyl myristate, dimethyl isosorbide, oleyl alcohol, labrafil, labrasol, medium chain triglyceride, diethyl sebacate, lanolin oil, citrate triisocetyl triglycerides having 10-18 carbon atoms, caprylic/capric triglycerides, coconut oil, corn oil, cottonseed oil, linseed oil, oil of mink, olive oil, palm oil, sunflower oil, nut oil, saturated paraffin oils, mineral oils, vegetable oils or glycerides, and the like. Solvent can also be selected from the group comprising monoalkyl ether of diethylene glycol such as diethylene glycol monomethyl ether, diethylene glycol monoethyl ether or mixtures thereof.

The term "emollients" refers to substances that soften and soothe the skin. They can be used to prevent dryness and scaling of the skin. Examples of emollients that can be used in the present peptide compositions include, but not limited to, oils of natural origin such as almond oil, coconut oil, olive oil, palm oil, peanut oil and the like, fatty acids such as lauric acid, myristic acid, palmitic acid, and stearic acid, monohydric alcohol esters of the fatty acids such as ethyl laurate, isopropyl laurate, ethyl myristate, n-propyl myristate, isopropyl myristate, ethyl palmitate, isopropyl palmitate, methyl palmitate, methyl stearate, ethyl stearate, isopropyl stearate, butyl stearate, isobutyl stearate, amyl stearate, and isoamyl stearate, glycols such as ethylene glycol, diethylene glycol, polyethylene glycol, branched aliphatic alcohols such as lauryl alcohol, myristyl alcohol, and stearyl alcohol, or mixtures thereof. Exemplary emollients include caprylic/capric triglyerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, gyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, silicones and mixtures thereof.

Silicones are typically organically modified organopoly siloxanes, sometimes called silicone surfactants. Useful polysiloxane or silicone emollients include, but not limited to, polysiloxane polymer, dimethicone copolyols, cyclomethicones. These materials are polydimethyl siloxanes, which have been modified to include polyether side chains such as polyethylene oxide chains, polypropylene oxide chains, mixtures of these chains, and polyether chains containing moieties derived from both ethylene oxide and propylene oxide.

The term "antioxidants" are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. Suitable antioxdants that can be used in the present peptide compositions include, but not limited to, ascorbic acid (vitamin C), glutathione, lipoic acid, uric acid, sorbic acid, carotenes, a-tocopherol (vitamin E), TPGS, ubiquinol, butylated hydroxyanisole, butylated hydroxytoluene, sodium benzoate, propyl gallate (PG, E310), and tertiary-butylhydroquinone.

The term "preservative" refers to a natural or synthetic chemical that prevents the decomposition of the composition by microbial growth or by undesirable chemical changes.

Preservatives can be incorporated into a peptide composition for protecting against the growth of potentially harmful microorganisms. While microorganisms tend to grow in an aqueous phase and can also reside in a hydrophobic or oil phase. Examples of preservatives that can be used in the present peptide compositions include, but are not limited to, methylparaben, propylparaben, benzyl alcohol, chlorocresol, benzalkonium chloride, cetrimonium chloride, sodium edetate, boric acid, sorbic acid, or any mixtures thereof.

The term "thickening agents" or "gelling agents" are used to give bulkiness to the peptide composition. Examples of thickening agents or gelling agents that can be used in the present peptide compositions include, but not are limited to: carbomers, polyethylene glycols, acrylate polymers, methacrylate polymers, polyvinylpyrrolidones, copolymers based on butyl methacrylate and methyl methacrylate povidone, vinyl acetates, polyvinyl acetates, celluloses, gums, alginates, cellulose acetate phthalates, cellulose acetate butyrates, hydroxypropyl methyl cellulose phthalates, and the like. Examples include CARBOPOL® products, PEG 400, EUDRAGIT® 100, EUDRAGIT® RSPO, EUDRAGIT® RLPO, EUDRAGIT® ND40, PLASDONE®, copolymers based on butyl methacrylate and methyl methacrylate (PLASTOID® B), alkyl celluloses such as ethyl celluloses and methyl celluloses, hydroxyalkyl celluloses such as hydroxyethyl cellulose and hydroxypropyl cellulose, hydroxyalkyl alkyl celluloses such as hydroxypropyl methyl celluloses and hydroxybutyl methyl celluloses, gums such as xanthan gum, tragacanth, guar gum, locust bean gum, acacia, and the like.

In an embodiment, the thickening agents can include non-polymeric thickening agents, such as fatty alcohols. Examples of fatty alcohols include, but are not limited to: cetyl alcohol, paraffin, stearyl alcohol, white wax, wax cetyl esters, microcrystalline wax, anionic emulsifying wax, non-ionic emulsifying wax, yellow wax, castor oil, ceresin, cetostearyl alcohol, cyclomethicone, glyceryl behenate, hectorite, myristyl alcohol, cetylstearyl alcohol, triolein, and lanolin. Other thickening agents or gelling agents or polymers that are useful in the present peptide compositions include, but not limited to, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, cellulose ethers, cellulose esters, nitrocelluloses, polymers of acrylic and methacrylic esters, cellulose acetates, cellulose propionates, cellulose acetate butyrates, cellulose acetate phthalates, carboxylethyl celluloses, cellulose triacetates, cellulose sulphate sodium salts, poly(methyl ethacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylenes, polypropylenes, poly(ethylene glycol), poly(ethylene oxide), poly(ethylene terephthalate), poly(vinyl alcohol), poly(vinyl acetate), poly(vinyl chloride), polystyrenes, and the like, including their mixtures thereof.

Examples of other useful polymers that can act as thickening agents or gelling agents include, but not limited to, synthetic polymers, such as polymers of lactic acid and glycolic acid, polyanhydrides, poly(ortho ester), polyurethanes, poly(butyric acid), poly(valeric acid), poly(caprolactone), poly(hydroxybutyrate), poly(lactide-co-glycolide), poly(lactide-co-caprolactone), and natural polymers such as alginate and other polysaccharides that include but not limited to arabinans, fructans, fucans, galactans, galacturonans, glucans, mannans, xylans (such as, for example, inulin), levan, fucoidan, carrageenan, galactocarolose, pectic acid, pectin, amylose, pullulan, glycogen, amylopectin, cellulose, dextran, pustulan, chitin, agarose, keratan, chondroitan, dermatan, hyaluronic acid, alginic acid, xanthan gum, starches, and various other natural homopolymers and heteropolymers, such as those containing one or more of aldoses, ketoses, acids or amines, erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof, and including dextran and cellulose, collagen, albumin and other hydrophilic proteins, zein and other prolamines and hydrophobic proteins, copolymers and mixtures thereof.

In some embodiments, the peptide compositions can further include one or more penetration enhancers. Penetration enhancers used in the topical compositions can provide higher skin layer retention and lower systemic exposure by avoiding the drug entering into systemic circulation, this tendency of the penetration enhancers provides skin depot compositions.

In some embodiments, the peptide composition can further include one or more antioxidant, preservative, humectant, or plasticizer.

It is contemplated that some of the excipient substances described above can have more than one function in a formulation. For example, a substance can be both a solvent and a penetration enhancer, or both a solvent and a carrier. The categorizations of materials described above are not to be construed as limiting or restricting in any manner.

Implementations of example targeting peptides are described below with research and methodologies following.

Targeting Peptide to Target 14-3-3 Dimerization to Reduce SCC Cell Viability

Figure 1A:
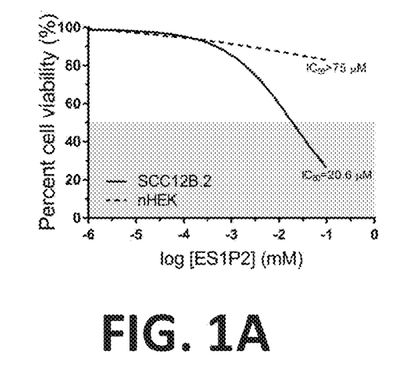
FIG. 1A is a dose response curve for a first targeting peptide (ES1P2) with respect to squamous cell carcinoma (SCC) cells in accordance with an example implementation of the present disclosure.
Figure 1B:
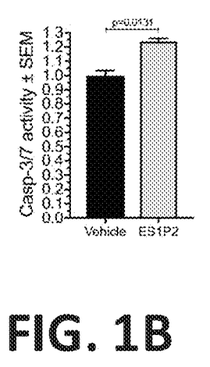
FIG. 1B shows Caspase-3/7 Glo assay results to determine apoptosis for SCC cells treated with vehicle or the first targeting peptide (ES1P2).

In embodiments, the targeting peptide includes a synthesized tetrapeptide, ES1P2 (Trp-Tyr-Trp-Lys-NH$_2$ (SEQ ID NO: 1)), configured to reduce 14-3-3ε dimerization and increase SCC apoptotic cell death. 14-3-3 proteins can function as oncogenes by promoting tumor-like characteristics such as cell survival, invasion, and proliferation, where 14-3-3 proteins are required for CDC25A-mediated suppression of apoptosis in skin cancers. Specifically, the 14-3-3ε isoform facilitates the activation of anti-apoptotic signaling pathways via Akt/BAD/Survivin signaling in SCC cells, where 14-3-3ε stabilizes Akt protein and sequesters Survivin into the cytoplasm of SCC cells. 14-3-3ε heterodimerization with other 14-3-3 isoforms is required for aspects of its activity. In SCC cells, 14-3-3ε preferentially forms heterodimers with 14-3-3γ and -ζ, and targeting 14-3-3ε heterodimerization with the targeting peptide ES1P2 reduced 14-3-3ε dimerization and increased SCC apoptotic cell death. Without wishing to be bound by any particular theory, ES1P2 targets N-terminal residues unique to 14-3-3ε to bind and reduce 14-3-3ε dimerization. FIG. 1A shows an example dose response curve for the targeting peptide ES1P2 with respect to SCC cells (SCC12B.2 cells) with an IC$_{50}$ of 20.6 μM. FIG. 1B shows an example Caspase-3/7 Glo assay (N=5) to determine apoptosis for SCC cells (SCC12B.2 cells) treated with vehicle or the targeting peptide ES1P2 (20 μM). The targeting peptide ES1P2 reduced 14-3-3ε heterodimerization, killed SCC cells but not normal keratinocytes, and decreased tumor growth.

Figure 1C:
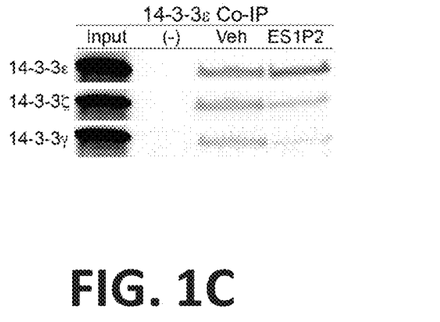
FIG. 1C is an immunoblot of immunoprecipitated 14-3-3ε protein from SCC12B.2 cells treated with vehicle or the first targeting peptide (ES1P2).

FIG. 1C shows an example immunoblot of immunoprecipitated 14-3-3ε protein from SCC12B.2 cells treated with vehicle (Tris buffer, pH 7.5) or ES1P2 (20 μM) for 48 hours. The control (−) included an equal number of cells incubated with IgG isotype control antibody. The immunoblot results indicate that ES1P2 reduces 14-3-3ε heterodimerization and induces SCC cell death by increasing apoptosis to a statistically significant degree (e.g., Student's two-tailed t-test, P≤0.05). Referring to FIG. 1A (dashed line) ES1P2 was nontoxic to normal keratinocytes. Without wishing to be bound by any particular theory, the altered localization of 14-3-3ε in SCC (cytoplasm) compared to normal skin (nuclear) can play a role in the ability of ES1P2 to induce SCC cell death while being nontoxic to normal keratinocytes.

Figure 1D:
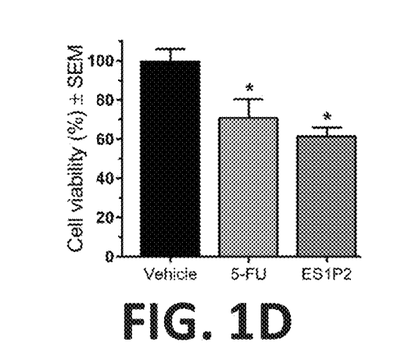
FIG. 1D shows Neutral Red Cell Viability assay results of the toxicity in SCC cells of the first targeting peptide (ES1P2) and an agent utilized for treatment of premalignant and malignant skin lesions.

In implementations, the targeting peptide ES1P2 exhibited greater toxicity in SCC cells as compared to the toxicity in SCC cells by an agent utilized for treatment of premalignant and malignant skin lesions, 5-Fluorouracil (5-FU). For example, FIG. 1D shows a comparative example via Neutral Red Cell Viability assay of the toxicity in SCC cells of ES1P2 and 5-FU, where ES1P2 alone was more effective in killing SCC cells (20 μM; 62% alive) than 5-FU alone (20 μM; 71.5% alive).

Figure 1E:
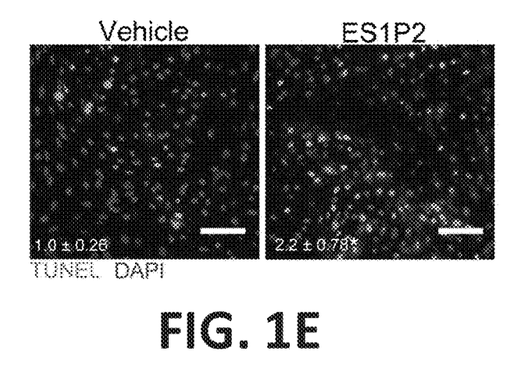
FIG. 1E shows TUNEL (terminal uridine nick-end labelling) assay results to detect apoptosis on whole tumor sections from vehicle-treated or ES1P2-treated mouse xenograft tumors.
Figure 1F:
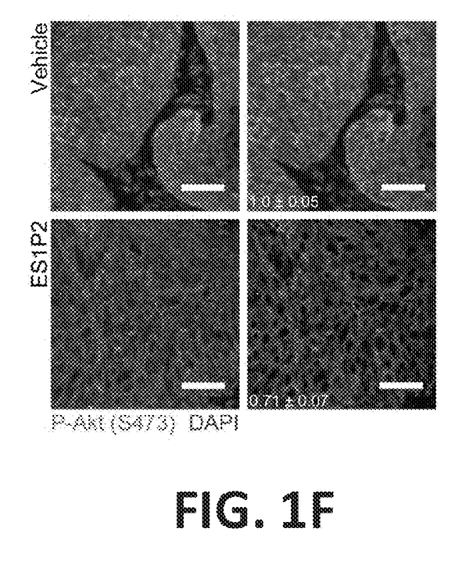
FIG. 1F shows immunofluorescence results for P-Akt (S473) in vehicle-treated and in ES1P2-treated SCC xenografts.
Figure 1G:
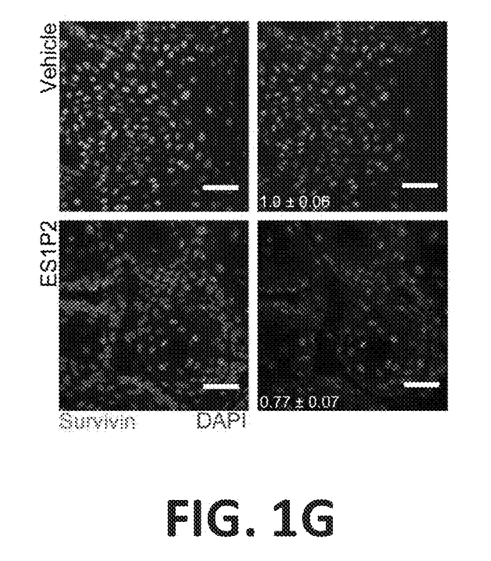
FIG. 1G shows immunofluorescence results for Survivin in vehicle-treated and in ES1P2-treated SCC xenografts.
Figure 1H:
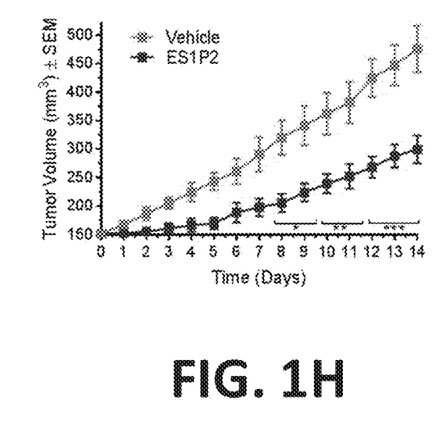
FIG. 1H shows a chart of tumor volume over time for vehicle-treated SCC cells and ES1P2-treated SCC cells.
Figure 1I:
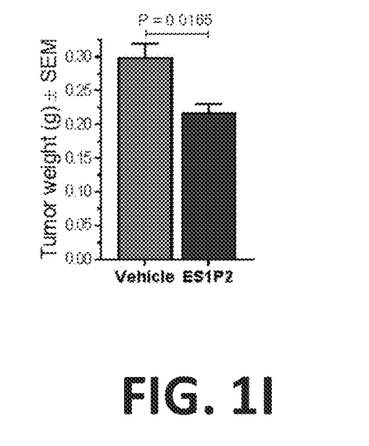
FIG. 1I shows a chart of tumor weight following dissection for vehicle-treated SCC cells and ES1P2-treated SCC cells.

In implementations, the targeting peptide ES1P2 decreased P-Akt (S473) and Survivin levels in ES1P2-treated SCC xenografts and reduced tumor volume in long-term treatments compared to vehicle-treated SCC xenografts. For example, FIG. 1E shows TUNEL (terminal uridine nick-end labelling) assays to detect apoptosis (FITC, green nuclei) on whole tumor sections from vehicle or ES1P2-treated mouse xenograft tumors with DAPI-labeled nuclei (blue) (scale bar=50 μm). The xenografts were established with a human skin cancer cell line and were treated intratumorally with either vehicle or 2.5 nmol of ES1P2. After 2 daily treatments, the number of TUNEL-positive SCC cells more than doubled compared to vehicle treated. Immunofluorescence revealed a decrease in P-Akt (S473) and Survivin levels in ES1P2-treated SCC xenografts. For example, FIG. 1F shows immunofluorescence results for P-Akt (S473) in vehicle-treated and in ES1P2-treated SCC xenografts and FIG. 1G shows immunofluorescence results for Survivin in vehicle-treated and in ES1P2-treated SCC xenografts. The targeting peptide ES1P2 also reduced SCC growth by approximately one-third as compared to vehicle-treated SCC cells following daily treatments of the SCC xenografts. For example, FIG. 1H shows a chart of tumor volume over time for vehicle-treated SCC cells and ES1P2-treated SCC cells and FIG. 1I shows a chart of tumor weight following dissection, which provides an example of in vivo application.

14-3-3ε promotes anti-apoptotic signaling in SCC cells and is critical for tumor development and progression in mouse skin. The targeting of 14-3-3ε heterodimerization with the targeting peptide ES1P2 effectively killed skin cancer cells and reduced tumor growth through targeting 14-3-3ε and reducing the ability of 14-3-3ε to form dimers.

Targeting Peptide to Target 14-3-3 Binding Sites of CDC25A to Reduce SCC Cell Viability In embodiments, the targeting peptide includes one or more synthetic phospho-peptide fragments to target one or two of the binding sites of CDC25A to 14-3-3ε. The phospho-peptide fragments can include, but are not limited to, peptide pS (phospho-Ser178; Ac-Thr-Gln-Arg-Gln-Asn-Ser-(PO$_3^{2-}$)-Ala-Pro-Arg-Met-Leu-Ser-Ser-Asn-NH$_2$ (SEQ ID NO: 2)) and peptide pT (phospho-Thr507 residue; Ac-Arg-Thr-Lys-Ser-Arg-Thr(PO$_3^{2-}$)-Trp-Ala-Gly-Glu-Lys-Ser-Lys-Arg-NH$_2$ (SEQ ID NO: 3)) to block 14-3-3ε binding to CDC25A and induce SCC cell death. SCC xenografted tumors treated with peptide pS and peptide pT displayed increased apoptotic cell death and decreased pro-survival P-Akt (S473) and Survivin. In vivo, mouse xenograft tumors treated with both peptide pS and peptide pT displayed decreased volume, increased apoptotic activity, and reduced P-Akt (S473) and Survivin expression in SCC cells compared to vehicle-treated tumors.

Figure 2A:
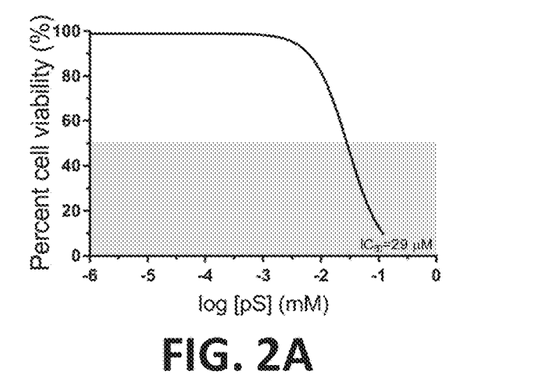
FIG. 2A is a dose response curve for a second targeting peptide (pS) with respect to SCC cells in accordance with an example implementation of the present disclosure.

Without wishing to be bound by any particular theory, peptide pS targets a first binding site of CDC25A (Ser178) and peptide pT targets a second binding site of CDC25A (Thr507) to block or otherwise inhibit interactions between CDC25A and 14-3-3ε to decrease SCC cell survival. Referring to FIG. 2A, an example dose response curve is shown for the targeting peptide pS with respect to SCC cells (SCC12B.2 cells) for twelve samples, with an $IC_{50}$ of 29 μM.

Figure 2B:
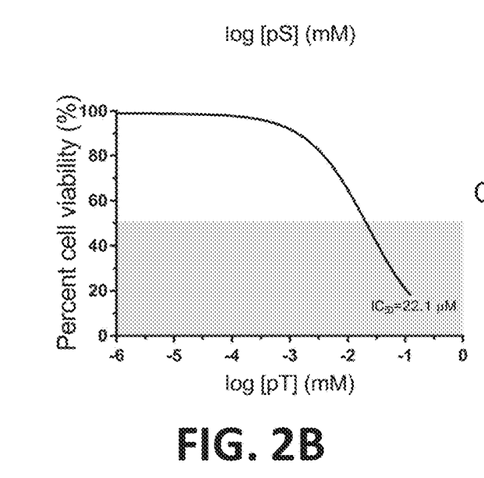
FIG. 2B is a dose response curve for a third targeting peptide (pT) with respect to SCC cells in accordance with an example implementation of the present disclosure.
Figure 2C:
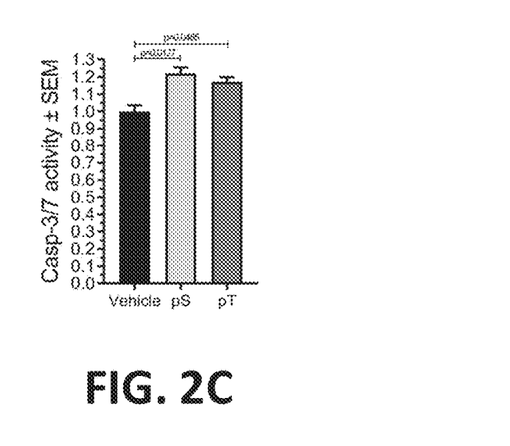
FIG. 2C shows a Caspase-3/7 Glo assay results to determine apoptosis for SCC cells treated with vehicle, the second targeting peptide (pS), or the third targeting peptide (pT).

Referring to FIG. 2B, an example dose response curve is shown for the targeting peptide pT with respect to SCC cells (SCC12B.2 cells) for twelve samples, with an $IC_{50}$ of 22.6 μM. FIG. 2C shows an example Caspase-3/7 Glo assay (N=5) to determine apoptosis for SCC cells (SCC12B.2 cells) treated with vehicle, the targeting peptide pS (30 μM), or the targeting peptide pT (20 μM) for 24 hours. Each of the targeting peptides (pS and pT) decreased SCC cell viability by increased apoptosis.

Figure 2D:
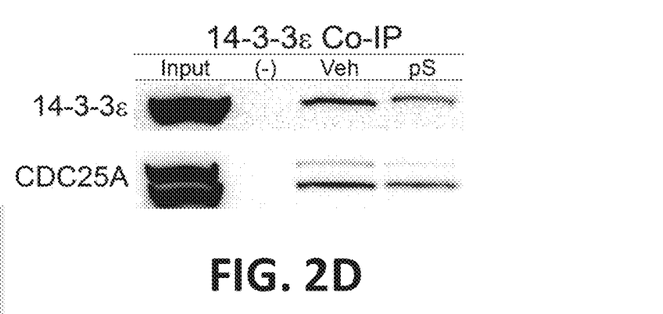
FIG. 2D is an immunoblot of immunoprecipitated 14-3-3ε protein from SCC12B.2 cells treated with vehicle or the second targeting peptide (pS).
Figure 2E:
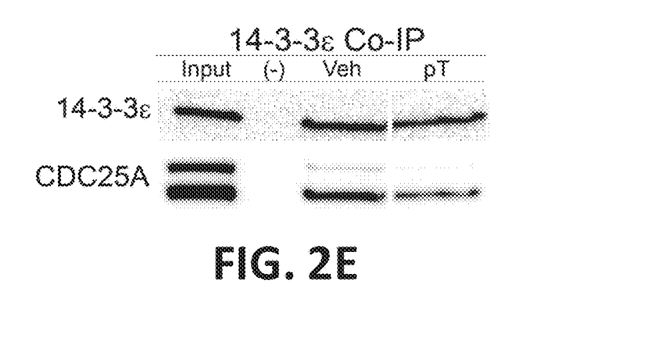
FIG. 2E is an immunoblot of immunoprecipitated 14-3-3ε protein from SCC12B.2 cells treated with vehicle or the third targeting peptide (pT).

FIG. 2D shows an example immunoblot of immunoprecipitated 14-3-3ε protein from SCC12B.2 cells treated with vehicle (Tris buffer, pH 7.5) or pS (30 μM) for 48 hours. The control (−) included an equal number of cells incubated with IgG isotype control antibody. The immunoblot results indicate that the targeting peptide pS decreases the amount of CDC25A present on the immunoblots when compared to immunoprecipitations from vehicle treated cells to a statistically significant degree (e.g., Student's two-tailed t-test, P≤0.05). FIG. 2E shows an example immunoblot of immunoprecipitated 14-3-3ε protein from SCC12B.2 cells treated with vehicle (Tris buffer, pH 7.5) or pT (20 μM) for 48 hours. The control (−) included an equal number of cells incubated with IgG isotype control antibody. The immunoblot results indicate that the targeting peptide pT decreases the amount of CDC25A present on the immunoblots when compared to immunoprecipitations from vehicle treated cells to a statistically significant degree (e.g., Student's two-tailed t-test, P≤0.05). In implementations, pS-treated samples showed less 14-3-3ε precipitation as compared to pT-treated samples.

Figure 3A:
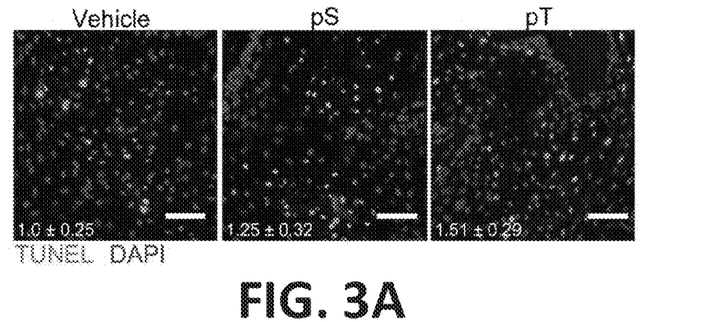
FIG. 3A shows TUNEL assay results to detect apoptosis on whole tumor sections from vehicle-treated, pS-treated, or pT-treated mouse xenograft tumors.
Figure 3B:
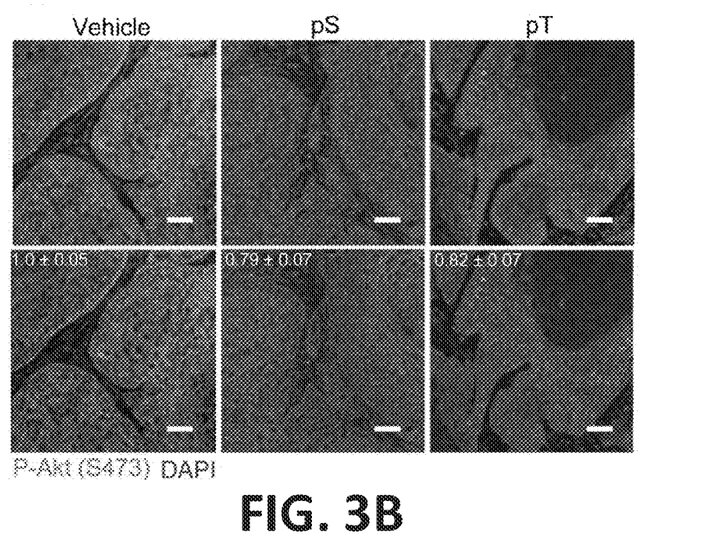
FIG. 3B shows immunofluorescence results for P-Akt (S473) in vehicle-treated, pS-treated, or pT-treated SCC xenografts.
Figure 3C:
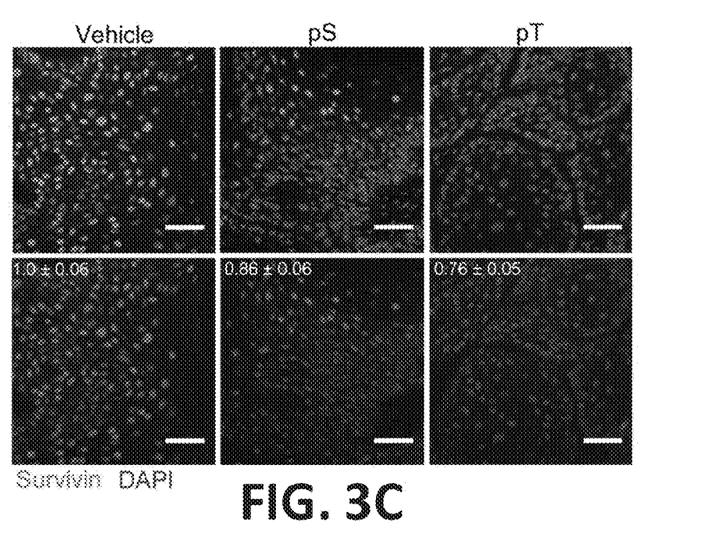
FIG. 3C shows immunofluorescence results for Survivin in vehicle-treated, pS-treated, or pT-treated SCC xenografts.

In implementations, the targeting peptides pS and pT each decreased Survivin and active Akt levels in targeting peptide-treated SCC xenografts as compared to vehicle-treated SCC xenografts. For example, FIG. 3A shows TUNEL (terminal uridine nick-end labelling) assays to detect apoptosis (FITC, green nuclei) on whole tumor sections from mouse xenograft tumors treated with vehicle, pS, or pT with DAPI-labeled nuclei (blue) (scale bar=50 μm). The xenografts were established with immunocompromised NCG mice injected with $5\times10^5$ SCC13 cells. After 2 daily treatments, the number of TUNEL-positive SCC cells increased by 25% and 51% in pS and pT treated tumors, respectively, when compared to vehicle treated tumors. Immunofluorescence revealed a decrease in P-Akt (S473) and Survivin levels in ES1P2-treated SCC xenografts. For example, FIG. 3B shows immunofluorescence results for P-Akt (S473) in vehicle-treated, pS-treated, and pT-treated SCC xenografts and FIG. 3C shows immunofluorescence results for Survivin in vehicle-treated, pS-treated, and pT-treated SCC xenografts.

CDC25A associates with 14-3-3ε, 14-3-3γ and 14-3-3ζ in SCC cells. CDC25A inhibits apoptosis by promoting the activation of Akt, inhibition of BAD, and an increase in Survivin, the same pathway that is regulated by 14-3-3ε. Treatment of SCC cells with the targeting peptides pS and pT reduced the interaction of 14-3-3ε with CDC25A, decreased SCC cell viability and increased apoptosis both in vitro and in vivo for each targeting peptide.

Methods and materials used in example diagnostic implementations of the above-described targeting peptides (ES1P2, pS, pT) are provided below.

Methods and Materials—ES1P2 Targeting Peptide Implementations

Cell Culture

Human skin cancer cell lines (SCC12B.2, SCC13, SRB12) were maintained in Dulbecco's modified Eagle's medium (DMEM) (Invitrogen, Carlsbad, CA, USA) supplemented with 1% penicillin (10000 U/ml)-streptomycin (10000 μg/ml) (PenStrep) (Invitrogen) and 10% fetal bovine serum (Gemini Bio-Products, Sacramento, CA, USA) at 37° C. and 5% $CO_2$. Normal human epidermal keratinocytes (nHEK) (Thermo Scientific, Waltham, MA, USA) isolated from neonatal foreskin were cultured in EpiLife medium (Invitrogen) supplemented with human keratinocyte growth supplement (Invitrogen) and 1% PenStrep (Invitrogen). Cells were transfected with control pcDNA or pcDNA3.1-HA-14-3-3ε (Addgene plasmid #48797; http://n2t.net/addgene:48797; RRID:Addgene_48797) using Lipofectamine/Plus reagents (Life Technologies, Carlsbad, CA, USA) or with siRNA targeting 14-3-3ε (Dharmacon, Lafayette, CO, USA), 14-3-3γ (Dharmacon), 14-3-3C, (Dharmacon), Survivin (Cell Signaling, Danvers, MA, USA), Akt (Dharmacon) or control siRNA (Santa Cruz Biotechnology, Dallas, TX, USA) using siQuest transfection reagents (Mirus Bio, Madison, WI, USA) or treated with Akt inhibitor GSK690693 (Tocris Bioscience, Bristol, United Kingom) or cell cycle inhibitor 5-Fluorouracil (5-FU) (Thermo Fisher) resuspended in DMSO.

Immunofluorescence and Immunohistochemistry

Immunostaining was performed using antibodies recognizing 14-3-3ε (Cell Signaling), 14-3-3γ (Cell Signaling), 14-3-3ζ (Cell Signaling), Survivin (Cell Signaling), P-Akt (S473) (Thermo Fisher), Keratin 5 (BioLegend, San Diego, CA, USA), Keratin 1 (BioLegend), Loricrin (Novus Biologicals, Centennial, CO, USA) or Ki67 (Abcam, Cambridge, UK). Immunohistochemistry was performed using horseradish peroxidase-conjugated secondary antibody (IgG rabbit) (Cell Signaling) with a hematoxylin (Sigma Aldrich, St. Louis, MO, USA) counterstain. Immunofluorescence was performed using an alexa-fluor488-conjugated secondary antibody (IgG mouse or rabbit) (Invitrogen) with 4',6-diamidino-2-phenylindole (DAPI) (Vector Labs, Burlingame, CA, USA) to identify nuclei. Cellular localization of immunohistochemistry signal was determined in a double-blinded manner. Slides were digitalized and fluorescence intensity was measured using Image analysis was performed using the Olympus VS120 Slide Scanner and Olyvia Analysis Software, respectively (Olympus, Tokyo, Japan).

Co-Immunoprecipitation

Co-Immunoprecipitation was performed using a Dynabeads Protein G Immunoprecipitation kit (Life Technologies, Carlsbad, CA, USA). Beads were coupled to antibodies targeting 14-3-3ε (Fisher Scientific, Waltham, MA, USA) or Akt (Thermo Fisher) at a ratio of 7 μg of antibody for every 1 mg of beads according to the manufacturers protocol. SCC12B.2 cells were treated with vehicle (20 mM Tris buffer, pH 7.5) or fresh ES1P2 targeting peptide daily at the $IC_{50}$ concentration for 48 hours in Opti-MEM I Reduced Serum Medium (Invitrogen) and collected by trypsinization. One hundred mg of cells were lysed in 1× IP buffer supplemented with 100 mM sodium chloride, 2 mM dithiothreitol, 1 mM magnesium chloride and protease (Roche Life Scientific, Penzberg, Germany) and phosphatase inhibitors (NaF, $Na_3VO_4$). Immunoprecipitation reactions were carried out using 1.5 mg of antibody-coupled beads incubated with 100 mg of cell lysate at 4° C. for 30 minutes. Negative controls were immunoprecipitation reactions using beads coupled to IgG isotype control antibody (rabbit), and whole lysate from immunoprecipitation input was loaded directly onto a gel was used as a positive control.

Immunoblotting

Protein was collected by either standard whole-cell lysis using ice-cold radioimmunoprecipitation assay (RIPA) lysis buffer supplemented with protease (Roche Life Scientific) and phosphatase inhibitors (NaF, $Na_3VO_4$) or by nuclear/cytosolic extraction using the NE-PER Nuclear and Cytoplasmic Protein Extraction Reagent Kit according to the manufacturer's protocol (Pierce, Rockford, IL, USA). Tissue protein was extracted by using a tissue grinder to lyse cells in 100 μL of RIPA lysis buffer for every 1 mg of tissue. Samples were centrifuged for 5 minutes to remove depleted tissue debris. Protein concentration was assessed with the Bradford assay. Protein lysates (30 ug/lane) were resolved on a 10% SDS-PAGE denaturing gel, transferred to a nitrocellulose membrane and blocked in 5% non-fat dry milk in 1× Tris buffered saline supplemented with 0.01% Tween 20. Immunoblotting was performed by incubating membranes overnight at 4° C. using antibodies to detect 14-3-3ε, β, η, γ, σ, θ or ζ (Cell Signaling for all), β-Akt (S473) (Cell Signaling), total Akt (Cell Signaling), P-Bad (S136) (Cell Signaling), total BAD (Cell Signaling) Survivin (Cell Signaling), MSIN3A (Abcam), GAPDH (Abcam) or a/p-tubulin (Cell Signaling). Bands were detected using horseradish peroxidase-conjugated secondary antibodies (IgG mouse or rabbit) (Cell Signaling) and visualized using western lightning plus chemiluminescent reagent (MidSci, Valley Park, MO, USA) and signal read on a Chemidoc XRS Molecular Imager (Bio-Rad Laboratories, Hercules, CA, USA).

Caspase-3/7 Glo Assay

Apoptosis was assessed using a Caspase-3/7 Glo assay (Promega Corporation, Madison, WI, USA) in a 96-well white-bottom plate (BRANDplates, Wertheim, Germany) according to the manufacturer's instructions. Cells were seeded at a density of $8×10^3$ cells/well and incubated overnight before treatments or transfections. Luminescence was read using a Cytation 5 multi-mode plate reader (BioTek Instruments, Winooski, VT, USA).

Cycloheximide Assay

SCC12B.2 cells were plated at equal cell densities ($5×10^5$ cells/plate) in 60 mm plates. Cells were first transfected with either control siRNA (Santa Cruz Biotechnology) or 14-3-3ε siRNA (Dharmacon). Forty-eight hours post-transfection the control siRNA transfected cells were treated with either vehicle (DMSO) or cycloheximide (100 μg/mL) (Abcam), while 14-3-3ε siRNA transfected cells were treated with 100 μg/mL cycloheximide for 8 or 24 hours. To ensure equal numbers of cells were used for immunoblotting, cells were collected by standard trypsinization, resuspended in 500 μL of 1×PBS and counted on a Countess II automated cell counter (Thermo Fisher) four separate times to obtain an average cell number. Protein was collected by lysing $1.5×10^6$ cells per treatment group. Equal volumes of cell lysate were used for immunoblotting detection.

Mouse Tumor Xenografts

Groups of NCG mice (NOD CRISPR Prkdc Il2r gamma/NjuCrl) (Charles River, Malvern, PA, USA) were injected s.c. with $5×10^5$ SCC13 cells suspended in 1:1 mixture of 1×PBS:Matrigel (Corning, Corning, NY, USA). Once the tumors reached a volume of 150 mm³, tumors were treated with either vehicle (50 μL 1×PBS) or 2.5 nmol/50 μL of the targeting peptide ES1P2. Tumors were injected directly with either vehicle or ES1P2 daily for 2 days or every other day for 2 weeks and then harvested for analysis 24 hours after the last treatment. Tumors were fixed overnight in 10% buffered formalin (Thermo Fisher) and then switched to 70% ethanol the following day. All procedures were performed in accordance with the guidance of Creighton University Institutional Animal Care and Use Committee.

14-3-3ε Conditional KO Mice Production

Conditional knockout of 14-3-3ε in the epidermis of the skin was achieved by crossing 14-3-3ε$^{fl/+}$ C57B16 mice with KRT14-Cre recombinase transgenic mice on an FVB/N background. Offspring were backcrossed onto FVB/N mice for five generations to reduce background heterogeneity. Genotyping for all mice was performed by polymerase chain reaction (PCR). To detect wild type and floxed alleles the following primers were used: aggtaccaaaacagtaagccatctcccta and gcatgtgtttgtctgtcagaggac. To detect the KO allele the following primers were used: and ttcttttgtagaaattggggaaggtcatgg. All procedures were performed in accordance with the guidance of Creighton University Institutional Animal Care and Use Committee.

Assessment of Epidermal Hyperplasia

Epidermal hyperplasia was evaluated using hematoxylin and eosin (H&E)-stained skin sections from the ventral surface of each mouse. The average epidermal thickness was determined by measuring from the outer edge of the most basal keratinocyte nucleus, to the edge of the outermost keratinocyte nucleus at eight randomly-selected locations along the length of each skin section per mouse in a double-blinded manner. The average number of epidermal cell layers was assessed by counting the number of nucleated cell layers at eight randomly-selected locations in each section in a double-blinded manner. Measurements and counts were done by using Olympus VS120 Slide Scanner Analysis Software (Olympus).

Chemical Carcinogenesis Protocol

At six weeks of age the dorsal hair of male and female 14-3-3ε WT and 14-3-3ε MT mice was clipped (N=20 WT, N=18 MT). Two days after clipping, 50 nmol of 7,12-dimethylbenz[a]anthracene (DMBA) (50 nmol/200 μL acetone) was topically applied. Two weeks after DMBA treatment the mice were treated once weekly with 6.8 nmol of 12-O-tetradecanoylphorbol-13-acetate (TPA) (6.8 nmol/200 μL in acetone) for 5 weeks. Following the five weeks of single TPA treatments, mice were treated 2 times per week with 6.8 nmol of TPA. Animals were weighed 3 times per week and tumors were counted once per week. Groups of mice were euthanized at 24, 27 or 30 weeks. Paraffin-embedded sections of each tumor were assessed for histopathology by two board-certified dermatologists. All procedures were performed in accordance with the guidance of the Creighton University Institutional Animal Care and Use Committee.

Tetrapeptide Library

Three-dimensional structures for the virtual tetrapeptide library were generated using the YASARA program. The library contained twenty standard amino acid residues, where cysteine was excluded to prevent synthetic problems at later stage ($19^4$=130,321 structures). Four different terminal end protection strategies were used in the library: free, N-acetyl, C-terminal amide and both termini capped (4×130,321=521,284 structures). A Python script was used to automate peptide generation and minimization in vacuo. Minimization in solvent was not utilized since the torsional angles are randomized during docking: bond lengths and angles were possible candidates for correction after initial structure generation.

Target Selection and Docking

The N-terminal region with residue Asp6, Tyr9 and Gln6 of 14-3-3ε, as unique residues among of the seven isoforms of 14-3-3 proteins, were identified as a binding site. The non-protein components in the X-ray structure of 14-3-3ε were deleted and missing H-atoms were added using YASARA. The resultant structure was relaxed in an aqueous environment using 200 ns Molecular Dynamics (MD) simulation. Binding site residues were assigned using the ray-tracing algorithm included in the Molegro Virtual Docker (MVD) program. Receptor grids were aligned to the geometric center of the identified binding sites and tetrapeptides were docked using the GPU screening module of MVD. Hits were clustered using Tabu clustering of MVD with root mean square deviation (RMSD) cutoff of 2.5 Å, ensuring maximum diversity in poses. Poses were ranked according to their molegro-derived energies; this scoring function is a modified version of PLANTS.

Molecular Dynamics (MD) Simulation

For MD simulations, the GROMACS-2016 package was used with the CHARMM36m force field. The structures of 14-3-3ε-peptide complex was solvated in a dodecahedron with TIP3P water molecules and 0.15 M sodium chloride. The system was subjected to 1000 steps steepest descent energy minimization and then to 1 ns constant number of molecules, volume and temperature (NVT) simulation at 300 K so that the position of the protein-peptide complex was constrained at the center of the dodecahedron with a force constant of 1000 kJ·mol$^{-1}$. The system was then equilibrated during a 10 ns unrestrained constant number of molecules, pressure and temperature (NPT) simulation at 1 bar pressure and 300 K temperature. The integration step was 2 fs, the LINCS algorithm was used to constrain all bonds to their correct length with a warning angle of 30°. The protein-peptide complex and the solvent with ions were coupled to separate temperature baths with a relaxation constant of 0.1 ps. The peptide and the solvent with ions were coupled separately to constant pressure with a relaxation constant of 1.0 ps and $4.5 \times 10^{-5}$ bar$^{-1}$ isothermal compressibility. The temperature was controlled by a stochastic velocity-rescaling method. The long-range electrostatic interactions were calculated using the PME method with 1.2 nm cutoff distance applying Verlet scheme and 0.15 nm Fourier spacing. For the calculations of van der Waals interactions the short-range and long-range cutoffs, respectively, were 1.0 and 1.2 nm using the force-switch modifier. Finally, 250 ns NPT was performed at 300 K and 1 bar pressure. The parameters were the same as during equilibrations, except the protein-peptide complex and solvent with ions were separately coupled to a 1 bar Parrinello-Rahman barostat. After the initial 250 ns screening those structures in which the peptides did not dissociate from the Tyr9 region of 14-3-3ε were further simulated for 2 ps using the same parameters as for the screening.

Residue Contribution Binding Energy

The residue contribution to the binding energy of peptides to 14-3-3ε for the last 50 ns of the 2 ps simulation was calculated using g_mmpbsa software. For the calculations solvent and solute dielectric constant were 80 and 4, respectively. Temperature and sodium chloride concentration were the same as in the simulations.

Peptide Production

Peptides were synthesized and purified to greater that 95% purity by Bachem (Bachem Americas Inc., Torrance, CA, USA) and EZBiolabs (EZBiolabs, Carmel, IN, USA).

Neutral Red Cell Viability Assay

To determine the half maximal inhibitory concentration (IC$_{50}$) for ES1P2 in SCC12B.2 and nHEK cells, cells were plated in a 96-well plate at a density of $6 \times 10^3$ cells/well. Twenty-four hours after plating, cells were treated with increasing concentrations of ES1P2 (0-75 µM) in Opti MEM medium supplemented with reduced serum (Invitrogen) for 4 consecutive days. ES1P2 peptide was resuspended fresh, daily in 25 mM Tris buffer (pH 7.5). Neutral Red Cell Viability assays were performed, where absorbance was measured using a Cytation 5 multi-mode plate reader (BioTek). The experiment was repeated three separate times with 4 replicate wells per experiment to obtain an average IC$_{50}$ value.

TUNEL Assay

TUNEL (Terminal deoxynucleotidyl transferase dUTP nick end labeling) was carried out using Promega DeadEnd Fluorometric TUNEL system in accordance with the manufacturer's instructions (Promega). Cells were treated with DAPI (Vector Labs) to locate the nuclei within cells. TUNEL-positive cells were those that displayed a clear nuclear signal. Slides were digitalized and apoptotic nuclei counted using an Olympus VS120 Slide Scanner (Olympus).

Statistical Analysis

Comparisons between two groups was performed using a two-tailed Student's t-test, where P≤0.05. Significance was determined using one-way ANOVA with the Dunnett's post-hoc test for comparison of more than two groups, where P≤0.05. For data collected at multiple time points, two-way ANOVA with a Bonferroni correction was used, where P≤0.05.

Methods and Materials—pS and pT Targeting Peptide Implementations

Cell Culture

Carcinoma human cell lines (SCC12B.2 and SCC13) were maintained in Dulbecco's modified Eagle's medium (DMEM) (Invitrogen, Carlsbad, CA, USA) supplemented with 1% penicillin (10000 U/ml)-streptomycin (10000 µg/ml) (PenStrep) (Invitrogen) and 10% fetal bovine serum (Gemini Bio-Products, Sacramento, CA, USA) at 37° C. and 5% CO2. Primary normal human epidermal keratinocytes (nHEK) (Thermo Fisher Scientific, Waltham, MA, USA) isolated from neonatal foreskin were maintained in EpiLife medium (Invitrogen) supplemented with human keratinocyte growth supplement (HKGS) and 1% PenStrep. nHEK cells were not passaged more than twice before experiments. Cells were treated with CDC25A inhibitor NSC663284 (Tocris Bioscience, Bristol, United Kingdom) suspended in DMSO, transfected with wild type CDC25A or control plasmid using Lipofectamine/Plus transfection reagents (Life Technologies, Carlsbad, CA, USA) or transfected with siRNA targeting 14-3-3ε or control siRNA (Santa Cruz Biotechnology, Dallas, TX, USA) using siQuest transfection reagents (Mirus Bio, Madison, WI, USA).

Peptide Structure and Molecular Dynamics Simulations

The pS and pT peptides include the 173-186 and 501-515 fragments of human CDC25 Å, respectively, and were digitally generated by the YASARA program. Peptide pS further includes the phospho-Ser178 (pSer) and pT further includes the phospho-Thr507 (pThr) residue. Residues of an existing peptide in the X-ray structure of 14-3-3ε were mutated to the corresponding CDC25A fragments residues. Both peptides were N-terminally acetyl- and C-terminally amide-protected to preserve the electronic structure of the backbone. The resultant structure was energy-minimized in gas phase using two steps: 1) the atoms of 14-3-3ε were frozen and the ligand peptide was relaxed; and 2) in a subsequent step the whole system was relaxed. Stability of the prepared peptide-14-3-3ε complexes was determined by molecular dynamics (MD) simulations using the GRO-MACS-2016 package and the CHARMM36m force field.

The structures of the 14-3-3δ-peptide complexes were solvated in a dodecahedron with TIP3P water molecules and 0.15 M sodium chloride. The system was subjected to 1000 steps steepest descent energy minimization and then to 1 ns constant number of molecules, volume and temperature (NVT) simulation at 300 K so that the position of the protein-peptide complex was constrained at the center of the dodecahedron with a force constant of 1000 kJ·mol$^{-1}$. The system was then equilibrated during 10 ns unrestrained constant number of molecules, pressure and temperature (NPT) simulation at 1 bar pressure and 300 K temperature. The integration step was 2 fs, the LINCS algorithm was used to constrain all bonds to their correct length with a warning angle of 30°. The peptide and the solvent with ions were coupled to separate temperature baths with a relaxation constant of 0.1 ps. The system was coupled to constant pressure with a relaxation constant of 1.0 ps and 4.5×10$^{-5}$ bar$^{-1}$ isothermal compressibility. The temperature was controlled by a stochastic velocity-rescaling method. The long-range electrostatic interactions were calculated using the PME method with 1.2 nm cutoff distance applying the Verlet scheme and 0.15 nm Fourier spacing. For the calculations of van der Waals interactions the short-range and long-range cutoffs, respectively, were 1.0 and 1.2 nm using the force-switch modifier. Finally, 1000 ns NPT simulation was performed at 300 K and 1 bar pressure. The parameters were the same as during equilibration, except that the temperature was kept constant by using leap-frog stochastic dynamics integrator with $\tau_T$ of 2 ps and the system was coupled to 1 bar Parrinello-Rahman barostat.

Trajectory Analysis

Configurational entropy was calculated to determine if thermodynamic equilibrium was reached. The covariance matrix for the Cα-atoms was calculated using the covar module of GROMACS, the eigenvectors corresponding to the 150 highest eigenvalues were used to calculate the backbone configurational entropy. Stability of the protein-peptide complex was determined by calculating the root-mean-square deviations (RMSD) of the Cα-atoms. Representative structures of the simulation were determined by using the GROMOS method of clustering with Cα-atoms RMSD cutoff of 0.2 nm using structures sampled in 100 ps intervals.

Peptide Production

Peptides were synthesized and purified to greater than 95% purity by Bachem (Bachem Americas Inc., Torrance, CA, USA) and EZBiolabs (EZBiolabs, Carmel, IN, USA).

Immunofluorescence

Immunostaining was performed using antibodies recognizing P-Akt (S473) (Thermo Fisher) and Survivin (Cell Signaling, Danvers, MA, USA), with alexa-fluor488-conjugated secondary antibody (IgG rabbit) (Invitrogen) with 4',6-diamidino-2-phenylindole (DAPI) (Vector Labs, Burlingame, CA, USA) to identify the nuclei. Slides were digitalized and analyzed using an Olympus VS120 Slide Scanner (Olympus, Shinjuku, Tokyo, JPN).

Co-Immunoprecipitation

Co-Immunoprecipitation (Co-IP) was performed using a Dynabeads Protein G Immunoprecipitation kit (Life Technologies, Carlsbad, CA, USA). Beads were coupled to antibodies targeting 14-3-3ε (Fisher Scientific, Waltham, MA, USA) or CDC25A (Santa Cruz Biotechnology, Dallas, TX, USA) at a ratio of 7 μg of antibody for every 1 mg of beads according to the manufacturers protocol. SCC12B.2 cells were treated with vehicle (20 mM Tris buffer, pH 7.5) or fresh peptide (pS or pT) daily at the IC$_{50}$ concentration for 48 hours in Opti-MEM I Reduced Serum Medium (Invitrogen) and collected by trypsinization. One hundred mg of cells were lysed in 1× IP buffer supplemented with 100 mM sodium chloride, 2 mM dithiothreitol, 1 mM magnesium chloride and protease/phosphatase inhibitors. Immunoprecipitation reactions were carried out using 1.5 mg of anti-body-coupled beads incubated with 100 mg of cell lysate at 4° C. for 30 minutes. Negative controls were immunoprecipitation reactions using beads coupled to IgG isotype control antibody (rabbit), and whole lysate from immunoprecipitation input was loaded directly onto a gel was used as a positive control.

Immunoblotting

Protein was collected by either standard whole-cell lysis using ice-cold radioimmunoprecipitation assay (RIPA) lysis buffer supplemented with protease (Roche Life Scientific) and phosphatase inhibitors (NaF, Na$_3$VO$_4$) or by nuclear/cytosolic extraction using the NE-PER Nuclear and Cytoplasmic Protein Extraction Reagent Kit according to the manufacturer's protocol (Pierce, Rockford, IL, USA). Tissue protein was extracted by using a tissue grinder to lyse cells in 100 μL of RIPA lysis buffer for every 1 mg of tissue. Samples were centrifuged for 5 minutes to remove depleted tissue debris. Protein concentration was assessed with the Bradford assay. Protein lysates (30 ug/lane) were resolved on a 10% SDS-PAGE denaturing gel, transferred to a nitrocellulose membrane and blocked in 5% non-fat dry milk in 1× Tris buffered saline supplemented with 0.01% Tween 20. Immunoblotting was performed by incubating membranes overnight at 4° C. using antibodies to detect 14-3-3ε, β, η, γ, σ, ↓ or ζ (Cell Signaling for all), CDC25A (Santa Cruz Biotechnology), β-Akt (S473) (Cell Signaling), total Akt (Cell Signaling), P-Bad (S136) (Cell Signaling), total BAD (Cell Signaling), Survivin (Cell Signaling), or GAPDH (Cell Signaling). Bands were detected using horseradish peroxidase-conjugated secondary antibodies (IgG mouse or rabbit) (Cell Signaling) and visualized using western lightning plus chemiluminescent reagent (MidSci, Valley Park, MO, USA) and signal read on a Chemidoc XRS Molecular Imager (Bio-Rad Laboratories, Hercules, CA, USA).

Apoptosis Antibody Array

Protein was extracted from SCC12B.2 cells using lysis buffer supplemented with protease and phosphatase inhibitors. SCC12B.2 cells were transfected with empty vector DNA or wild-type CDC25A for 48 hours, or control (Santa Cruz Biotechnology) or 14-3-3ε siRNA for 48 hours (Dharmacon). Array membranes (Cell Signaling), containing antibodies against 19 pro- and anti-apoptotic proteins were incubated with whole-cell lysates overnight at 4° C. according to the manufacturer's instructions. Immunoreactive dots were visualized using western lightning plus chemiluminescent detection system (MidSci) to generate a signal on a Chemidoc XRS Molecular Imager (Bio-Rad Laboratories).

Mouse Tumor Xenografts

Groups of NCG mice (NOD CRISPR Prkdc Il2r gamma/NjuCrl) (Charles River, Malvern, PA, USA) were injected s.c. with 5×10$^5$ human SCC13 cells suspended in 1:1 mixture of 1× PBS:Matrigel (Corning, Corning, NY, USA). Once the tumors reached 150 mm$^3$ in volume they were treated intratumorally with either vehicle (1x sterile PBS, pH, 7.5), pS, or pT (2.5 nmol/50 μL for each) daily for 2 days and then the mice were euthanized 24 hours after the second treatment. Tumors were fixed overnight in 10% neutral buffered formalin (Thermo Fisher) and then switched to 70% ethanol the following day before embedding and sectioning. All procedures were performed in accordance with the guidance of the Creighton University Institutional Animal Care and Use Committee.

TUNEL Assay

TUNEL (terminal uridine nick-end labelling) assays were carried out using the Promega DeadEnd Fluorometric TUNEL system in accordance with the manufacturer's instructions (Promega Corporation, Madison, WI, USA). Cells were treated with 4',6-diamidino-2-phenylindole (DAPI) to locate the nuclei within cells. Slides were scanned and analyzed using an Olympus VS120 Slide Scanner (Olympus).

Caspase-3/7 Glo Assay

Apoptosis was assessed using a Caspase-3/7 Glo assay (Promega) in a 96-well white-bottom plate (BRANDplates, Wertheim, Germany). Cells were seeded at a density of $8 \times 10^3$ cells/well and Caspase-3/7 glo was performed 24 hours post-treatment according to the manufacturer's instructions and read using a Cytation 5 multi-mode plate reader (BioTek, Instruments, Winooski, VT, USA).

Neutral Red Cell Viability Assay

To determine the half maximal inhibitory concentration ($IC_{50}$) for pS and pT in SCC12B.2 cells, cells were plated in a 96-well plate at a density of $6 \times 10^3$ cells/well. Twenty-four hours after plating cells were treated with increasing concentrations of pS and pT peptides (0-75 μM) in Opti MEM media supplemented with reduced serum (Invitrogen) for 4 consecutive days. The peptides were resuspended fresh daily in 20 mM Tris buffer (pH 7.5). Neutral Red Cell Viability assays were performed, where absorbance was measured using a Cytation 5 multi-mode plate reader (BioTek). The experiment was repeated three separate times with 4 replicate wells in each experiment to obtain an average $IC_{50}$ value.

Statistical Analysis

Significance was determined using one-way ANOVA with the Dunnett's post-hoc test for comparison of more than two groups, where P≤0.05. Comparisons between two groups were performed using a two-tailed Student's t-test, where P≤0.05.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

The invention claimed is:

1. An isolated peptide having activity against squamous cell carcinoma survival, the peptide comprising a structure as set forth in SEQ ID NO: 3.

2. The isolated peptide of claim 1, further comprising a pharmaceutically acceptable carrier.

3. The isolated peptide of claim 1, further comprising one or more of an emulsion, a lotion, a cream, a gel, or an emollient.

4. The isolated peptide of claim 2, wherein the pharmaceutically acceptable carrier is suitable for administration via at least one of administration via injection, topical administration, aerosol administration, administration via inhalation, oral administration, systemic IV application, ocular administration, and rectal administration.

5. The isolated peptide of claim 2, wherein the pharmaceutically acceptable carrier includes a water-immiscible solvent.

* * * * *

UNITED STATES PATENT AND TRADEMARK OFFICE
CERTIFICATE OF CORRECTION

PATENT NO. : 12,122,852 B2
APPLICATION NO. : 18/076033
DATED : October 22, 2024
INVENTOR(S) : Laura Hansen, Sandor Lovas and Nicholas Palermo Page 1 of 1

It is certified that error appears in the above-identified patent and that said Letters Patent is hereby corrected as shown below:

On the Title Page

Item (71) Applicant, Please change "The Board of Regents of the University of Nebraska, Omaha, NE (US)" to "Nutech Ventures, Lincoln, NE (US)"

Signed and Sealed this
Twenty-sixth Day of August, 2025

Coke Morgan Stewart
*Acting Director of the United States Patent and Trademark Office*

SEQUENCE LISTING

```
Sequence total quantity: 3
SEQ ID NO: 1            moltype = AA  length = 4
FEATURE                 Location/Qualifiers
REGION                  1..4
                        note = Synthetic peptide
MOD_RES                 4
                        note = C-terminal amidation
source                  1..4
                        mol_type = protein
                        organism = synthetic construct
SEQUENCE: 1
WYWK                                                                    4

SEQ ID NO: 2            moltype = AA  length = 14
FEATURE                 Location/Qualifiers
REGION                  1..14
                        note = Synthetic peptide
MOD_RES                 1
                        note = ACETYLATION N-terminal acetylation
MOD_RES                 6
                        note = PHOSPHORYLATION Phosphorylation of SER
MOD_RES                 14
                        note = AMIDATION C-terminal amidation
source                  1..14
                        mol_type = protein
                        organism = synthetic construct
SEQUENCE: 2
TQRQNSAPRM LSSN                                                        14

SEQ ID NO: 3            moltype = AA  length = 14
FEATURE                 Location/Qualifiers
REGION                  1..14
                        note = Synthetic peptide
MOD_RES                 1
                        note = ACETYLATION N-terminal Acetylation
MOD_RES                 6
                        note = PHOSPHORYLATION Phosphorylation of Thr
MOD_RES                 14
                        note = AMIDATION C-terminal amidation
source                  1..14
                        mol_type = protein
                        organism = synthetic construct
SEQUENCE: 3
RTKSRTWAGE KSKR                                                        14
```